United States Patent
Satou et al.

(10) Patent No.: US 10,577,577 B2
(45) Date of Patent: Mar. 3, 2020

(54) DEVICE FOR MANUFACTURING ORGANIC SUBSTANCE AND METHOD FOR MANUFACTURING ORGANIC SUBSTANCE

(71) Applicant: SEKISUI CHEMICAL CO., LTD., Osaka (JP)

(72) Inventors: Kanetomo Satou, Ibaraki (JP); Yoji Fujimori, Ibaraki (JP); Tetsuya Ishii, Ibaraki (JP); Kokoro Hamachi, Ibaraki (JP); Kazuo Doyama, Ibaraki (JP)

(73) Assignee: SEKISUI CHEMCIAL CO., LTD., Osaka (JP)

( * ) Notice: Subject to any disclaimer, the term of this patent is extended or adjusted under 35 U.S.C. 154(b) by 486 days.

(21) Appl. No.: 14/917,697

(22) PCT Filed: Sep. 12, 2014

(86) PCT No.: PCT/JP2014/074258
§ 371 (c)(1),
(2) Date: Mar. 9, 2016

(87) PCT Pub. No.: WO2015/037710
PCT Pub. Date: Mar. 19, 2015

(65) Prior Publication Data
US 2016/0222340 A1     Aug. 4, 2016

(30) Foreign Application Priority Data

Sep. 13, 2013  (JP) ................................ 2013-190617
Feb. 25, 2014  (JP) ................................ 2014-033868
(Continued)

(51) Int. Cl.
*C10K 1/04* (2006.01)
*C12P 7/08* (2006.01)
(Continued)

(52) U.S. Cl.
CPC ................ *C12M 47/10* (2013.01); *C10J 3/82* (2013.01); *C10K 1/002* (2013.01); *C10K 1/02* (2013.01);
(Continued)

(58) Field of Classification Search
CPC ...... C12M 21/00; C12M 21/12; C12M 47/10; C12P 7/08
See application file for complete search history.

(56) References Cited

U.S. PATENT DOCUMENTS 5,866,091 A * 2/1999 Stevenson ................ C01B 3/36
                                                     252/373
2007/0221541 A1 * 9/2007 McClanahan ........... C07B 63/00
                                                     208/263
(Continued)

FOREIGN PATENT DOCUMENTS

JP    2012-001441    1/2012
JP    2012-149089    8/2012
(Continued)

OTHER PUBLICATIONS

Do et al. "Growth of Rhodospirillum rubrum on Synthesis Gas: Conversion of CO to H2 and Poly-B-hydroxyalkanoate." Biotechnology and Bioengineering, vol. 97, No. 2 (Jun. 1, 2007), pp. 279-286. (Year: 2007).*
(Continued)

*Primary Examiner* — William H. Beisner
(74) *Attorney, Agent, or Firm* — Wenderoth, Lind & Ponack, L.L.P.

(57) ABSTRACT

Provided is a novel apparatus capable of suitably manufacturing an organic substance from a syngas. An apparatus 1 for manufacturing an organic substance includes a syngas producing furnace (11), an organic substance synthesis unit (16), a moisture content raising unit (12), and a moisture
(Continued)

content lowering unit (13). The syngas producing furnace (11) is configured to produce a syngas containing carbon monoxide by partly oxidizing a carbon source. The organic substance synthesis unit (16) is configured to produce an organic substance from the syngas. The moisture content raising unit (12) is disposed between the syngas producing furnace (11) and the organic substance synthesis unit (16). The moisture content raising unit (12) is configured to raise a moisture content of the syngas. The moisture content lowering unit (13) is disposed between the moisture content raising unit (12) and the organic substance synthesis unit (16). The moisture content lowering unit (13) is configured to lower the moisture content of the syngas.

7 Claims, 1 Drawing Sheet

(30) Foreign Application Priority Data

Feb. 28, 2014 (JP) ................................ 2014-038384
Mar. 6, 2014 (JP) ................................ 2014-044443

(51) Int. Cl.
| | | |
|---|---|---|
| *C12M 1/00* | (2006.01) | |
| *C10L 1/02* | (2006.01) | |
| *C10K 1/02* | (2006.01) | |
| *C10J 3/82* | (2006.01) | |
| *C10K 1/00* | (2006.01) | |
| *C10K 1/10* | (2006.01) | |

(52) U.S. Cl.
CPC ............... *C10K 1/04* (2013.01); *C10K 1/101* (2013.01); *C10K 1/103* (2013.01); *C10L 1/023* (2013.01); *C12M 21/00* (2013.01); *C12M 21/12* (2013.01); *C12M 43/00* (2013.01); *C12P 7/08* (2013.01); *C10J 2300/1659* (2013.01); *C10J 2300/1665* (2013.01); *C10J 2300/1681* (2013.01); *C10J 2300/1846* (2013.01); *C10L 2290/04* (2013.01); *C10L 2290/08* (2013.01); *C10L 2290/26* (2013.01); *C10L 2290/547* (2013.01)

(56) References Cited

U.S. PATENT DOCUMENTS

| | | | | |
|---|---|---|---|---|
| 2012/0291351 | A1* | 11/2012 | Bool ....................... | C01B 3/36 48/197 FM |
| 2013/0137151 | A1* | 5/2013 | Tobey ....................... | C01B 3/36 435/161 |
| 2013/0149755 | A1 | 6/2013 | Reed et al. | |
| 2014/0272734 | A1* | 9/2014 | Braun ....................... | C10K 1/04 431/11 |

FOREIGN PATENT DOCUMENTS

| | | |
|---|---|---|
| WO | 2009/058028 | 5/2009 |
| WO | 2009/154788 | 12/2009 |
| WO | 2010/126382 | 11/2010 |
| WO | 2011/087380 | 7/2011 |

OTHER PUBLICATIONS

International Preliminary Report on Patentability dated Mar. 15, 2016 in International Application No. PCT/JP2014/074258 (p. 1).
Written Opinion dated Dec. 16, 2014 in International Application No. PCT/JP2014/074258 (English Translation).
International Search Report dated Dec. 16, 2014 in International (PCT) Application No. PCT/JP2014/074258.
Yukimoto et al., "Haikibutsu-kei Biomass no Yuko Riyo to sono Genjo in Kansuru Gijutsu Chosa Hokoku", Panel Discussion & Tokubetsu, Koen Haikibutsu-kei Biomass no Yuko Riyo no Genjo -Mokushitsu-kei Biomass-, Nov. 21, 2008, pp. 1-1 to 1-31, pp. 1-6, 1-11, fig. 3-2, partial English translation.
Extended European Search Report dated Apr. 7, 2017 in corresponding European Application No. 14843678.5.
Meier, "Using Venturi Scrubber Technology for Syngas Cleaning", APC (2013), 3 pgs. https://www.bionomicind.com/pdf/apc_UsingVenturiScrubberTechnology for Syngas.pdf.
Bartocci, "Wet Scrubbers for Gasifier Gas Cleaning", Paper #49 (1998) http://www.elmiraohio.com/Gasifier Docs/Wet_Scrubbers.pdf.
Tashikazu Ooya et al., Chapter V. Demonstration Plan for Reforming Biogas and Introducing Energy Equipment, Report for Betsukai-cho Biomass Utilization Plan, pp. 99-114 (2006), with Partial Translation.
Munasinghe P.C. and Kharial S. K., "Syngas Fermentation to Biofuel: Evaluation of Carbon Monoxide Mass Transfer ,.Coefficient (kLa) in Different Reactor Configurations", Biotechnology Progress, 26(6): 1616-1621 (2010).
Wang et al. "Dust and Toxic Gas Control Technology", Inner Mongolia University Press, p. 181 (2012).
Office Action dated Sep. 10, 2018 in Chinese Application No. 201480049178.3, with English-language translation of Search Report.

* cited by examiner

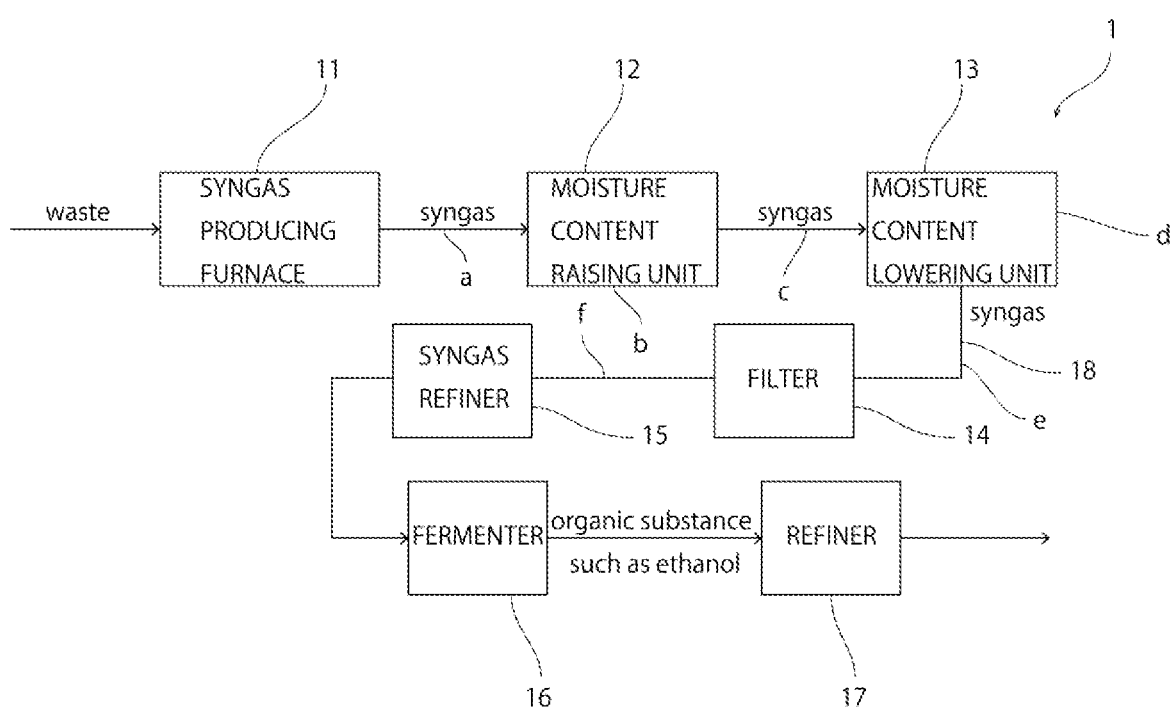

DEVICE FOR MANUFACTURING ORGANIC SUBSTANCE AND METHOD FOR MANUFACTURING ORGANIC SUBSTANCE

TECHNICAL FIELD

The present invention relates to an apparatus for manufacturing an organic substance and a method for manufacturing an organic substance.

BACKGROUND ART

In recent years it has been considered to put into practical use a method for manufacturing a chemical substance, such as ethanol, by microbially fermenting a carbon monoxide-containing syngas synthesized from exhaust gas or the like emitted from, for example, a steel plant (see, for example, Patent Literature 1).

CITATION LIST

Patent Literature

Patent Literature 1: WO2011/087380

SUMMARY OF INVENTION

Technical Problem

However, an apparatus for manufacturing an organic substance from a syngas has not currently been put into practical use and, in reality, has not been sufficiently considered.

A principal object of the present invention is to provide a novel apparatus capable of suitably manufacturing an organic substance from a syngas.

Solution to Problem

An apparatus for manufacturing an organic substance according to the present invention includes a syngas producing furnace, an organic substance synthesis unit, a moisture content raising unit, and a moisture content lowering unit. The syngas producing furnace is configured to produce a syngas containing carbon monoxide by partly oxidizing a carbon source. The organic substance synthesis unit is configured to produce an organic substance from the syngas. The moisture content raising unit is disposed between the syngas producing furnace and the organic substance synthesis unit. The moisture content raising unit is configured to raise a moisture content of the syngas. The moisture content lowering unit is disposed between the moisture content raising unit and the organic substance synthesis unit. The moisture content lowering unit is configured to lower the moisture content of the syngas.

In the apparatus for manufacturing an organic substance according to the present invention, the moisture content raising unit is preferably further configured to pass the syngas through water.

In the apparatus for manufacturing an organic substance according to the present invention, the moisture content raising unit is preferably further configured to raise the moisture content of the syngas until an amount of moisture in the syngas reaches a saturated amount of water vapor.

In the apparatus for manufacturing an organic substance according to the present invention, the syngas producing furnace is preferably further configured to produce the syngas containing carbon monoxide by partly oxidizing waste containing the carbon source.

The apparatus for manufacturing an organic substance according to the present invention preferably further includes a filter disposed between the moisture content lowering unit and the organic substance synthesis unit and configured to remove a solid content in the syngas.

In the apparatus for manufacturing an organic substance according to the present invention, the moisture content lowering unit is preferably further configured to lower the moisture content of the syngas by cooling the syngas using a refrigerant or lowering a dew point of the syngas using a membrane dryer. Alternatively, the moisture content lowering unit may be formed using an adsorbent or a water adsorbent.

In the apparatus for manufacturing an organic substance according to the present invention, the organic substance synthesis unit preferably contains a microorganism capable of producing the organic substance from the syngas by fermentation.

The apparatus for manufacturing an organic substance according to the present invention may further include a pipe connecting between the syngas producing furnace and the organic substance synthesis unit. The moisture content lowering unit is preferably disposed upstream of a portion of the pipe reachable to a lowest temperature in the pipe and configured to remove moisture in the syngas so that an amount of moisture in the syngas is smaller than a saturated amount of water vapor in the portion of the pipe reachable to the lowest temperature when the portion is at the lowest temperature.

In the apparatus for manufacturing an organic substance according to the present invention, the moisture content lowering unit is more preferably further configured to cool the syngas to below the lowest temperature in the pipe. Alternatively, the moisture content is lowered by the membrane dryer so that the syngas has a dew point lower than the lowest temperature in the pipe.

In a method for manufacturing an organic substance according to the present invention, a syngas producing step is performed of producing a syngas containing carbon monoxide by partly oxidizing a carbon source. A moisture content raising step is performed of raising a moisture content of the syngas. The raised moisture content of the syngas is lowered. An organic substance is produced from the syngas lowered in moisture content.

In the method for manufacturing an organic substance according to the present invention, the syngas is preferably passed through water in the moisture content raising step.

In the method for manufacturing an organic substance according to the present invention, an amount of moisture in the syngas is preferably a saturated amount of water vapor in the moisture content raising step.

In the method for manufacturing an organic substance according to the present invention, a moisture content lowering step may be further performed of removing moisture in the syngas, upstream of a portion of a pipe reachable to a lowest temperature in the pipe, the pipe connecting between a syngas producing furnace and an organic substance synthesis unit, so that an amount of moisture in the syngas is smaller than a saturated amount of water vapor in the portion of the pipe reachable to the lowest temperature when the portion is at the lowest temperature.

In the method for manufacturing an organic substance according to the present invention, the syngas is preferably cooled to below the lowest temperature in the pipe in the moisture content lowering step.

Advantageous Effects of Invention

The present invention can provide a novel apparatus capable of suitably manufacturing an organic substance from a syngas.

BRIEF DESCRIPTION OF DRAWINGS

The FIGURE is a schematic diagram of an apparatus for manufacturing an organic substance from waste according to one embodiment of the present invention.

DESCRIPTION OF EMBODIMENTS

Hereinafter, a description will be given of an exemplary preferred embodiment for working of the present invention. However, the following embodiment is simply illustrative. The present invention is not at all limited to the following embodiment.

The FIGURE is a schematic diagram of an apparatus for manufacturing an organic substance from waste according to this embodiment. A manufacturing apparatus 1 shown in the FIGURE is an apparatus for manufacturing an organic substance from waste containing a carbon source, such as waste plastic, household garbage or biomass. The organic substance manufactured may be an oxygen-containing organic matter. The organic substance manufacture may be, for example, alcohol, organic acid, fatty acid, fat, ketone, biomass or sugar. Specific examples of alcohol, organic acid, fatty acid, fat, ketone, biomass, and sugar that can be cited include ethanol, acetic acid, butanediol, acetone, and butanol.

No particular limitation is placed on the application of the manufactured organic substance. The manufactured organic substance can be used as a raw material for plastic, resin or the like or can be used as a fuel.

The manufacturing apparatus 1 includes a syngas producing furnace 11, a moisture content raising unit 12, a moisture content lowering unit 13, a filter 14, a syngas refiner 15, a fermenter 16, and a refiner 17. The syngas producing furnace 11 is supplied with waste containing an organic matter containing a carbon source, such as plastic or resin. In the syngas producing furnace 11, the waste is partly oxidized to produce a syngas containing carbon monoxide. Normally, the syngas contains, in addition to carbon monoxide, hydrogen gas, nitrogen gas, and carbon dioxide.

Normally, waste contains food garbage or the like. Therefore, the waste has a high moisture content. For this reason, the syngas produced by partly oxidizing the waste has a high moisture content as compared to a syngas emitted from, for example, a steel plant.

However, in the present invention, the syngas producing furnace need not necessarily be a furnace configured to produce a syngas by partly oxidizing waste. The syngas producing furnace may be, for example, a gas producing furnace using coal, coke or oil shale as a source material or a vapor methane reforming furnace using a natural gas or the like as a source material.

The syngas produced in the syngas producing furnace 11 is fed to the fermenter 16 serving as an organic substance synthesis furnace. The fermenter 16 contains a microorganism and a culture medium. The culture medium contains salts, vitamins, essential amino acids, and essential metal ions which are necessary for microbial augmentation. The microorganism ferments to produce an organic substance from the syngas. Therefore, in the fermenter 16, an organic substance is manufactured from the syngas by microbial fermentation. Examples that can be cited as the microorganism producing an organic substance from a syngas include carboxydotrophic bacteria. Specific examples of microorganisms that can be suitably used to produce alcohol, such as ethanol, include the genus *Clostridium*, the genus *Moorella*, and the genus *Veillonella*.

A description will be given in this embodiment of an example where the organic substance synthesis unit is composed of a fermenter. However, the present invention is not limited to this. The organic substance synthesis unit may be, for example, one that produces an organic substance from a syngas by a catalytic reaction of a metal catalyst or the like.

The fermenter 16 is connected to the refiner 17. The product in the fermenter 16 is transferred to the refiner 17. Normally, the fermenter 16 produces, in addition to an organic substance intended to be manufactured, other organic substances. The refiner 17 is configured to refine the product in the fermenter 16. Thus, a desired organic substance can be obtained.

Arranged between the syngas producing furnace 11 and the fermenter 16 are the moisture content raising unit 12, the moisture content lowering unit 13, and the filter 14 in this order from the syngas producing furnace 11 side. The moisture content raising unit 12, the moisture content lowering unit 13, and the filter 14 have the function of reducing the impurity concentration in the syngas. Further provision of the syngas refiner 15 enables the removal of impurities which may interfere with fermentation.

Impurities in the syngas are substances having adverse effects on the microbial metabolic reaction or the catalytic activity of a metal catalyst and examples thereof that can be cited include, but depending upon the type of microorganism or metal catalyst, aromatic compounds, saturated hydrocarbons, and unsaturated hydrocarbons. For example, the aromatic compounds include benzene, toluene, and xylene. The saturated and unsaturated hydrocarbons include C1 and higher hydrocarbons. The unsaturated hydrocarbons include C2 and higher hydrocarbons. Other impurities include sulfides and nitrogen compounds. Examples include carbonyl sulfide, hydrogen sulfide, SOx, and NOx. Other impurities also include cyanogen compounds, acids, and alkalis.

Materials for use as the filter include a HEPA filter, an activated carbon filter, a zeolite filter, and a non-woven fabric filter. In terms of structure, the filter may be a filter made by combining and processing various filters. Furthermore, a photocatalyst, such as titanium oxide, may be processed for the filter.

The moisture content raising unit 12 is configured to raise the moisture content of the syngas. No particular limitation is placed on the method for raising the moisture content of the syngas. For example, water vapor may be fed to the syngas or water may be sprayed into the syngas. In this embodiment, the moisture content of the syngas is raised by passing the syngas through water in the moisture content raising unit 12. The moisture content raising unit 12 allows moisture in the syngas to substantially reach a saturated amount of water vapor.

The moisture content raising unit 12 is connected to the moisture content lowering unit 13. The moisture content lowering unit 13 is configured to remove moisture from the syngas to lower the moisture content of the syngas raised by the moisture content raising unit 12. The moisture content lowering unit 13 is preferably configured to cool the syngas into dew to lower the moisture content of the syngas. No particular limitation is placed on the method for cooling the syngas. For example, the syngas may be cooled using a refrigerant. Alternatively, the moisture in the syngas may be removed using a moisture adsorbent, such as a molecular sieve. The moisture may be reduced by bringing the syngas into contact with a refrigerant to allow condensed water to be trapped. The moisture may be removed by lowering the partial pressure of the syngas to condense the moisture. Alternatively, a membrane separation device may be provided, such as a membrane dryer in which a moisture-permeable membrane is used, and the moisture may be removed by passing the syngas through the membrane separation device. Examples that can be cited as the method for bringing the syngas into contact with a cooling refrigerant include a cooling method in which a highly thermally conductive metal pipe is exposed to the outside air and a cooling method in which a refrigerant circulator is brought into contact with the gas. The moisture content lowering unit 13 may be configured to perform membrane dehydration.

The moisture content lowering unit 13 does not necessarily need to reduce the moisture content of the syngas to zero. No particular limitation is placed on the type of the moisture content lowering unit 13 so long as it can reduce the moisture content of the syngas.

The filter 14 is disposed between the moisture content lowering unit 13 and the fermenter 16. The filter 14 is configured to remove the solid content in the syngas. The filter 14 may be configured to remove the total solid content in the syngas or remove part of the solid content. In other words, the filter 14 is not limited to one that completely removes the solid content in the syngas. The solid content left unremoved is additionally removed in the syngas refiner 15. The solid content in the syngas refers to components, including tar, fly ash, and soot. Furthermore, with the use, as the filter 14, of a filter with an activated carbon filter incorporated thereinto, substances that cannot be removed by the moisture content raising unit 12 and the moisture content lowering unit 13 can also be removed in addition to the removal of the solid content.

As thus far described, in the apparatus 1 for manufacturing an organic substance, the moisture content of a syngas is first raised in the moisture content raising unit 12. Thereafter, in the moisture content lowering unit 13, water in the syngas is removed, so that the moisture content of the syngas decreases. In the step of removing the moisture in the syngas after raising the moisture content of the syngas in the above manner, water-soluble impurities and the solid content, such as tar and soot, contained in the syngas are removed together with water from the syngas. Therefore, a syngas of low impurity concentration can be fed to the fermenter 16. Thus, it can effectively be prevented that impurities have adverse effects on microorganisms. With the use of, for example, a catalyst in place of microorganisms, it can effectively be prevented that impurities have adverse effects on the catalyst. Hence, the apparatus 1 for manufacturing an organic substance can manufacture an organic substance with high efficiency.

Furthermore, since at least some of the impurities is removed in advance of the filter 14, the filter 14 can be prevented from clogging. Therefore, the replacement frequency of the filter can be reduced. As a result, the manufacturing efficiency of the organic substance can be increased to reduce the manufacturing cost.

From the viewpoint of more effectively removing impurities in a syngas, it is preferred to reduce the moisture content of the syngas after raising the moisture content of the syngas until the amount of water vapor in the syngas reaches a saturated amount of water vapor. By doing so, the amount of water removed from the syngas in the step of lowering the moisture content is increased, so that a larger amount of impurities can be removed.

Furthermore, from the viewpoint of more effectively removing impurities in a syngas, it is preferred to raise the moisture content of the syngas bypassing the syngas through water. The reason for this is that during passage of the syngas through water, water-soluble impurities are dissolved in the water and thus removed from the syngas and part of the solid content in the syngas moves into the water and is thus removed from the syngas.

The techniques for efficiently removing impurities contained in a syngas in this embodiment are also suitable in the case of use of any syngas. Among syngases, a syngas synthesized from waste may contain a large amount of impurities. Therefore, the techniques for efficiently removing impurities contained in the syngas in this embodiment are particularly suitable in the case of use of the syngas synthesized from waste.

Although no particular limitation is placed on the method for reducing the moisture content of a syngas, use is more preferably made of the method of reducing the moisture content of a syngas by cooling the syngas using a refrigerant. The reason for this is that a solid content-containing syngas can be suitably cooled.

The inventors attempted to actually manufacture an organic substance using a syngas synthesized from waste. In those experiments, the inventors unexpectedly encountered the problem of the feed of the syngas to the fermenter having stopped. It has been found from the inventors' intensive studies that because the syngas synthesized from waste had a high moisture content unlike syngases synthesized by a steel plant and the like, moisture in the syngas was condensed and frozen in the pipe to clog the pipe, so that the feed of the syngas to the fermenter stopped.

To cope with this, in the manufacturing apparatus 1, the moisture content lowering unit 13 is disposed in the pipe 18 connecting between the syngas producing furnace 11 and the fermenter 16 serving as an organic substance synthesis unit. The moisture content lowering unit 13 is disposed upstream of a portion of the pipe 18 reachable to the lowest temperature in the pipe 18. The moisture content lowering unit 13 is configured to remove moisture in a syngas so that the amount of moisture in the syngas is smaller than the saturated amount of water vapor in the portion of the pipe 18 reachable to the lowest temperature when the portion is at the lowest temperature. Specifically, in this embodiment, the moisture content lowering unit 13 is configured to remove moisture in the syngas by cooling the syngas to below the lowest temperature in the pipe 18. For example, a portion of the pipe 18 located outdoors can be cooled to the lowest temperature in winter at the location where the manufacturing apparatus 1 is installed. Therefore, the lowest temperature of the portion of the pipe 18 reachable to the lowest temperature in the pipe 18 is the lowest temperature in winter at the location where the manufacturing apparatus 1 is installed, and more preferably the lowest temperature in winter recorded thereat in the past ten years. Since the moisture content lowering unit 13 is provided in the manufacturing apparatus 1, even if the pipe 18 is cooled in winter, the pipe 18 can be prevented from dew formation and thus prevented from being clogged by freezing. Therefore, the syngas can be stably fed to the fermenter 16. Hence, with the use of the manufacturing apparatus 1, an organic substance can be stably manufactured.

From the viewpoint of enabling more stable manufacture of an organic substance, the moisture content lowering unit 13 is preferably configured to remove moisture in a syngas so that the amount of moisture in the syngas is smaller than 70% relative humidity of the saturated amount of water vapor in the portion of the pipe 18 reachable to the lowest temperature when the portion is at the lowest temperature, and more preferably configured to remove moisture in a syngas so that the amount of moisture in the syngas is smaller than 50% relative humidity of the same. For example, the moisture content lowering unit 13 is preferably configured to remove moisture from a syngas by cooling the syngas to or below 20° C. and more preferably configured to remove moisture from a syngas by cooling the syngas to or below 10° C. However, if the cooling temperature is too low, the energy required to cool the syngas is too much, which may reduce the energy efficiency for manufacturing an organic substance. Therefore, the cooling temperature of the syngas in the moisture content lowering unit 13 is preferably equal to or higher than a temperature about 5° C. lower than the lowest temperature in the pipe 18. Specifically, for example, the cooling temperature of the syngas in the moisture content lowering unit 13 is preferably not less than 15° C.

The fermentation of microorganisms in the fermenter 16 is an exothermic reaction. Therefore, if the fermenter 16 is not cooled, the temperature inside the fermenter 16 becomes too high, so that the fermentation efficiency of microorganisms may be low.

For example, it is conceivable to cool the fermenter 16 by disposing, around the fermenter 16, a pipe through which a coolant flows. In this case, however, it is difficult to sufficiently cool the central portion of the fermenter 16. For example, if the central portion of the fermenter 16 is cooled to a temperature suitable for fermentation, the temperature of a peripheral portion of the fermenter 16 may be lower than the temperature suitable for fermentation. Therefore, IL is difficult to maintain the entire fermenter 16 at the temperature suitable for fermentation.

Furthermore, since waste contains much moisture, a syngas derived therefrom has a high moisture content. If the syngas having a high moisture content is fed to the fermenter 16 and the temperature of the syngas is reduced in the fermenter 16, dew may be formed in the syngas. Because dew formation is an exothermic reaction, the dew formation in the fermenter 16 may further raise the temperature of the fermenter 16.

In this embodiment, after the moisture content of the syngas produced in the syngas producing step is lowered, the syngas lowered in moisture content is fed to the fermenter 16. Therefore, the water in the fermenter 16 is easily evaporated and taken into the syngas. This water evaporation is an endothermic reaction. Therefore, in this embodiment in which water evaporation easily occurs in the fermenter 16, the fermenter 16 is suitably cooled from inside with the water evaporation. Hence, it is not necessarily needed to separately provide a mechanism for cooling the fermenter 16. Furthermore, since the fermenter 16 can be cooled from inside, the temperature uniformity in the interior of the fermenter 16 can be increased. Therefore, the entire fermenter 16 can be maintained at a temperature suitable for fermentation. Hence, a high fermentation efficiency can be achieved. As a result, the manufacturing efficiency of the organic substance can be increased.

From the viewpoint of further increasing the temperature uniformity in the fermenter 16, it is preferred to feed the syngas lowered in moisture content to the microorganisms in the water of the fermenter 16 by bubbling. It is more preferred to bubble the syngas lowered in moisture content from the bottom surface of the fermenter 16. By doing so, water evaporation can be promoted over a wider region of the fermenter 16.

Furthermore, from the viewpoint of more efficiently cooling the fermenter 16, the syngas is preferably fed at a lower temperature than the fermenter 16 and more preferably fed at a temperature 10° C. lower than a set value of the fermentation temperature in the fermenter 16.

For example, if a syngas having a high temperature and a high amount of moisture is fed to the fermenter 16, moisture in the syngas may be condensed into dew in the fermenter 16 to increase the amount of water in the fermenter 16. If the amount of water in the fermenter 16 increases, the concentration of microorganisms in the fermenter 16 decreases, which may decrease the fermentation efficiency.

Unlike the above, in this embodiment, a syngas lowered in moisture content is fed to the fermenter 16. Therefore, it is possible to reduce the decrease of the concentration of microorganisms in the fermenter 16 and the attendant decrease of the fermentation efficiency.

EXAMPLE

A syngas exhausted from a waste incinerator was used as a source gas and the source gas was passed through a wet scrubber (manufactured by Kyoritsu Seisakusho Ltd.). Pure water or sodium carbonate was used in the scrubber. The temperature of the syngas having passed through the scrubber was measured by a hygrometer (TEKHNE Corporation).

The syngas having passed through the scrubber was passed through a mist separator (manufactured by MIURA CHEMICAL EQUIPMENT CO., LTD.) and part of the syngas was then allowed to flow through a sample gas dehumidifier (manufactured by IAC Co., Ltd.) at a flow rate of 8 NL/min. A dehumidification operation was performed so that the set value of the humidity of the syngas before the entry into the dehumidifier was 100% and the syngas reached each of humidities of 5%, 15%, 50%, and 80%.

Each dehumidified syngas was passed through a filter holder (having an inside diameter of 20 cm and a thickness of 5 cm) equipped with a dust collecting filter (VILEDON air filter PH-400 manufactured by Japan Vilene Company, Ltd.). After this series of experiments was continuously operated for about two weeks, various pieces of data in each process were measured. The data items on which the measurement was made are shown in Tables 1 and 2. Table 2 shows physical properties of filters two weeks after the start of the operation. In the tables, "N.T." is an abbreviation of Not Test (not analyzed).

TABLE 1

| MEASUREMENT ITEM | Measurement Locations Shown in the FIGURE | | | | | |
|---|---|---|---|---|---|---|
| | a | b | c | d | e | f |
| Ammonia Concentration in Air (ppm) | 18 | N.T. | 3 | N.T. | off-scale low | N.T. |
| Hydrogen Chloride Concentration in Air (ppm) | 0.32 | N.T. | off-low | N.T. | off-scale low | N.T. |
| Tar Concentration in Air (mg/m$^3$) (0° C. 101.3 kPa) | 870 | N.T. | 87 | N.T. | 10 | N.T. |
| Solid Content Residue in Liquid (mg/L) | N.T. | 1500 | N.T. | 500 | N.T. | N.T. |

TABLE 1-continued

| MEASUREMENT ITEM | Measurement Locations Shown in the FIGURE | | | | | |
|---|---|---|---|---|---|---|
| | a | b | c | d | e | f |
| $NH^{4+}$ Concentration (mg/L) | N.T. | 200 | N.T. | 10 | N.T. | N.T. |
| Cl Concentration (mg/L) | N.T. | 30 | N.T. | 2 | N.T. | N.T. |

TABLE 2

| MEASUREMENT ITEM | FILTER LIFE |
|---|---|
| Control (Fresh) | Not Clogged |
| Gas Humidity after Dehumidification at d in the FIGURE (5%) | Not Clogged |
| Gas Humidity after Dehumidification at d in the FIGURE (15%) | Not Clogged |
| Gas Humidity after Dehumidification at d in the FIGURE (50%) | 10 days |
| Gas Humidity after Dehumidification at d in the FIGURE (80%) | 10 days |
| No Moisture Content Lowering Unit (100% Gas Humidity) | 1 day |

REFERENCE SIGNS LIST

1: manufacturing apparatus
11: syngas producing furnace
12: moisture content raising unit
13: moisture content lowering unit
14: filter
15: syngas refiner
16: fermenter (organic substance synthesis unit)
17: refiner
18: pipe

The invention claimed is:

1. A method for manufacturing an organic substance, comprising:
 producing a syngas containing carbon monoxide by partly oxidizing a carbon source;
 raising a moisture content of the syngas;
 lowering the raised moisture content of the syngas;
 evaporating water of a culture medium in a fermenter by feeding the syngas lowered in moisture content to the fermenter, the fermenter comprising a microorganism and a culture medium;
 cooling inside of the fermenter due to the evaporation of the water; and
 producing an organic substance from the syngas by fermentation using the mircoorganism.

2. The method for manufacturing an organic substance according to claim 1, wherein the moisture content of the syngas is raised while passing the syngas through water.

3. The method for manufacturing an organic substance according to claim 1, wherein an amount of moisture in the syngas after raising the moisture content of the syngas and before lowering the raised moisture content of the syngas is a saturated amount of water vapor.

4. The method for manufacturing an organic substance according to claim 1, further comprising:
 feeding the syngas in a pipe connected to the fermenter after lowering the raised moisture content of the syngas,
 wherein lowering the raised moisture content of the syngas comprises:
 removing the moisture content of the syngas so that an amount of moisture in the syngas is smaller than a saturated amount of water vapor at the lowest temperature in the pipe.

5. The method for manufacturing an organic substance according to claim 4, wherein the raised moisture content of the syngas is lowered while cooling the syngas to below the lowest temperature in the pipe.

6. The method for manufacturing an organic substance according to claim 1, wherein the raised moisture content of the syngas is lowered while removing water-soluble impurities contained in the syngas whose moisture content is raised in raising the moisture content of the syngas together with the moisture content.

7. The method for manufacturing an organic substance according to claim 1, wherein a temperature of the syngas is lower than a temperature inside the fermenter when feeding the syngas lowered in moisture content to the fermenter.

* * * * *